(12) United States Patent
Dawley (10) Patent No.: US 7,748,069 B2
(45) Date of Patent: Jul. 6, 2010

(54) MULTIMEDIA TOOTHBRUSH (TOOTHPIX)

(76) Inventor: Cynthia A Dawley, 13 W. Holly St., Cranford, NJ (US) 07016

( * ) Notice: Subject to any disclaimer, the term of this patent is extended or adjusted under 35 U.S.C. 154(b) by 720 days.

(21) Appl. No.: 11/300,788

(22) Filed: Dec. 15, 2005

(65) Prior Publication Data
US 2007/0136964 A1 Jun. 21, 2007

(51) Int. Cl.
*A46B 15/00* (2006.01)
*A61C 17/22* (2006.01)
(52) U.S. Cl. .................. 15/22.1; 15/105; 434/263; 340/539.1; 340/573.1; 340/665
(58) Field of Classification Search .................. 15/22.1, 15/105; 434/263
See application file for complete search history.

(56) References Cited

U.S. PATENT DOCUMENTS

| 4,698,869 | A | * | 10/1987 | Mierau et al. ................. 15/22.1 |
| 4,716,614 | A | * | 1/1988 | Jones et al. ................... 15/105 |
| 4,787,847 | A | | 11/1988 | Martin | |
| 4,995,131 | A | | 2/1991 | Takeda | |
| 5,138,733 | A | | 8/1992 | Bock | |
| 5,189,751 | A | | 3/1993 | Giuliani | |
| 5,500,970 | A | | 3/1996 | Maurer | |
| 5,561,881 | A | * | 10/1996 | Klinger et al. ................ 15/22.1 |
| 5,613,259 | A | | 3/1997 | Craft | |
| 5,623,746 | A | | 4/1997 | Ichiro | |
| 6,190,167 | B1 | | 2/2001 | Sharp | |
| 6,475,173 | B1 | | 11/2002 | Bachman | |
| 6,517,348 | B1 | | 2/2003 | Ram | |
| 6,731,213 | B1 | * | 5/2004 | Smith ....................... 340/573.1 |
| 6,821,119 | B2 | | 11/2004 | Shortt | |
| 2006/0040246 | A1 | * | 2/2006 | Ding et al. .................. 434/263 |

FOREIGN PATENT DOCUMENTS

DE 19506129 * 8/1996

* cited by examiner

*Primary Examiner*—Mark Spisich
(74) *Attorney, Agent, or Firm*—Greenberg Traurig, LLP (57) ABSTRACT

Disclosed is an electric toothbrush for use with wireless devices. A pressure sensor coupled to a wireless transmitting device determines whether the electric toothbrush is being utilized correctly. When the toothbrush is utilized correctly, the wireless transmitter sends a signal to a receiving device which displays an appropriate output. When the toothbrush is not utilized correctly, the transmitter ceases transmitting a signal and the output from the receiver ceases to be displayed.

11 Claims, 5 Drawing Sheets

FIG. 1

PRIOR ART

FIG. 2

PRIOR ART

MULTIMEDIA TOOTHBRUSH (TOOTHPIX)

FIELD OF THE INVENTION

The invention relates generally to the field of toothbrushes. More specifically, the current invention is directed to an electric toothbrush that is wirelessly coupled to an electronic media output device.

BACKGROUND OF THE INVENTION

There are many benefits to brushing your teeth. First and foremost, tooth decay can be prevented by this practice. Brushing also prevents gum disease, which is a primary agent in decaying and lost teeth.

Healthy teeth make dental and orthodontic appointments shorter and more enjoyable, because there is less that needs to be done. Time and money are saved in the long run by keeping up plaque control in good dental hygienic practice. In addition, prevention of gum disease and or cavities results in avoiding unnecessary, costly procedures. Brushing can also help prevent bad breath by ridding the mouth of the bacteria that cause bad breath. Good oral care helps contribute to your overall health by promoting upkeep and maintenance.

Most dental professionals recommend that removal of plaque from tooth surfaces is best accomplished by brushing on a daily basis from home by using some form of "between the teeth" cleaning. The effectiveness of this type of cleaning is primarily a function of three independent variables: the user's brushing motion, the duration of the brushing, and the force (i.e., pressure) applied to the teeth during brushing. Theses three independent variables are subjective. For example, individual users may be more sensitive to pressure. Accordingly, such a user is more apt to apply less pressure on the teeth, which results in inefficient brushing technique.

To compensate for the subjective nature of brushing techniques, dental professionals have devised tools in an attempt to standardize the brushing process. For example, electric toothbrushes are well known. These brushes typically contain a detachable brush head coupled to a plastic housing. The housing contains a motor, a battery, and circuitry which power the brush head. This standardizes the brushing motion for a particular user. In addition, other types of electric brushes are known which utilize sonic vibrations in the brush head. These brushes are constructed in the same manner as a simple electric toothbrush. That is, sonic toothbrushes have a brush head coupled to a casing which contains a battery, a motor and other circuitry. However, in addition to the simple mechanical motion of the toothbrush, sonic pulses are sent which improve the brushing capabilities of the electric toothbrush.

Most sonic toothbrushes contain a rechargeable battery. The battery is recharged by a base or docking station which also acts as a cradle for the toothbrush. This allows the electric toothbrush to be wireless.

In addition, sonic toothbrushes and electric toothbrushes sometimes contain a pressure sensor in the head of the toothbrush. This sensor determines the amount of force applied to a user's teeth during the brushing process. It is preprogrammed to shut down power to the brush head if the force applied is outside of a specified range. As a result, a toothbrush with a pressure sensor can standardize the amount of pressure applied to a user's teeth during the brushing process.

In addition, some of these toothbrushes are equipped with a timer that notifies a user once the recommended cleaning time has elapsed. Currently, the recommended cleaning time is two minutes. This interval can be subdivided, so that an operator is notified of the time allotted to clean the lower and upper teeth. Alternatively, the interval can be subdivided into other intervals to account for other brushing quadrants. As a result, electric toothbrushes with a timer attempt to standardize the duration of the brushing process.

However, there are numerous deficiencies associated with this type of timer. Initially, a user is typically notified by an audio signal. This signal is very faint and can be very difficult to hear when the toothbrush is powered up and in a user's mouth.

Importantly, the signal does not motivate a user to adequately clean his or her teeth. Instead, it merely provides a prompt during the brushing process to either stop brushing or to change quadrants (e.g., move from the lower teeth to the upper teeth). This is especially problematic for individuals with a short attention span such as children. Unmotivated users tend to brush their teeth in an inefficient manner. As a result, teeth are not cleaned properly. This can lead to tooth decay or gingivitis.

Accordingly, there is a clear need in the art for an electric toothbrush that motivates an individual to properly brush his or her teeth for the appropriate duration of time.

SUMMARY OF THE INVENTION

The present invention overcomes the preceding deficiencies by providing an improved electric toothbrush system. The system comprises an electric toothbrush, a wireless transmitter, and a receiver.

Electric toothbrushes are well known in the art. For example, U.S. Pat. No. 6,798,169, herein incorporated by reference, describes a basic rechargeable electric toothbrush. The toothbrush comprises a brush head attached to a housing. The housing contains a power source such as a rechargeable battery, a motor to power the brush head, and an integrated circuit to control the operation of the brush head.

The brush head of the present invention further comprises a pressure sensor as is known in the art. Importantly, the pressure sensor is coupled to a wireless transmitter via the integrated circuit contained in the toothbrush housing. The pressure sensor acts as a power switch for the wireless device. In short, if the pressure sensor detects force outside of a predetermined range, a signal is sent which both disables the power source (i.e., the battery) and causes the transmitter to cease transmitting a signal.

Transmitters are well known in the art. By way of non-limiting examples, any of the following transmitters may be used in accordance with the present invention: GSM, ISDN, Ethernet, CATV, WiFi, any type of LAN, Bluetooth, or the like. Of course, any type of transmitter can be utilized in accordance with the present invention.

The transmitter sends a signal to an output device. Output devices are well known. Non-limiting examples of output devices which can be utilized in accordance with the present invention include a cellular telephone, a portable digital assistant, a digital media storage device, a digital media playback device, a digital media transmitting device, a digital media receiving device, an iPod®, a Blackberry®, television, DVD player, a personal computer, a laptop computer, and a video game console system. It is contemplated that the system of the present invention can be adapted to incorporate any type of output device, In operation, the user of the electric toothbrush in accordance with the present invention first turns on a power switch on the housing of the electric toothbrush. Current from the power source is delivered to the motor which drives the brush head. When a user begins brushing by applying the brush head to teeth, the pressure sensor measures the amount of force applied to a user's teeth. If the pressure is within a predetermined range (i.e., the amount of force applied is appropriate), a signal is sent to the transmitter. This signal authorizes the transmitter to transmit data and/or a signal. Conversely, if the pressure is not within the predetermined range, a signal is sent to the transmitter causing the transmitter to cease sending a signal and/or data.

The receiver, which is associated with the transmitter, receives the signal and/or data from the transmitter and responds appropriately. Typically, the signal will initiate power in the device, causing it to display its output for the appropriate brushing time (e.g., two minutes).

Advantageously, this allows a user to access the output while brushing his or her teeth. For example, when a child begins brushing his or her teeth, a signal could be sent to a video playback device such as a DVD. As long as the child applies the appropriate force to his or her teeth, the DVD player will play the video disk, which can contain a cartoon or the like. Since the DVD will stop playing the cartoon if the child uses the inappropriate amount of force, he or she is motivated to continue to brush properly so that the video can be watched.

The present invention also comprises a system in which a user can download output from an independent source. For example, a Bluetooth enabled digital playback device can download music, cartoons, movies, news, or other information from a remote database. After downloading the information, it can be displayed while a user brushes his or her teeth in a manner as previously described.

In accordance with the foregoing, it is an object of the invention to create an improved electric toothbrush which is coupled to an output device.

Yet another object of the present invention is to provide a toothbrush system that motivates children to brush their teeth for the appropriate amount of time.

Still another object of the current invention is to provide an improved electric toothbrush which is wirelessly coupled to an output device.

Further, it is an object of the present invention to provide an improved electric toothbrush which is wirelessly coupled to a video output device.

Yet another object of the present invention to provide an improved electric toothbrush which is wirelessly coupled to an audio output device.

Still another object of the present invention to provide an improved electric toothbrush which is wirelessly coupled to video game output device.

Still another object of the present invention to provide an improved electric toothbrush which is capable of wirelessly downloading and playing back audio data from a remote source.

Yet another object of the present invention to provide an improved electric toothbrush which is capable of wirelessly downloading and playing back video data from a remote source.

Further, it is an object of the present invention to provide an improved electric toothbrush which monitors the efficacy of a user's brushing technique.

Yet another object of the present invention is to provide an improved electric toothbrush which displays at least one output in response to a user's tooth brushing technique.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention. Reference is now made of the drawings in which:

DETAILED DESCRIPTION OF THE PREFERRED EMBODIMENT

A detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein that define the scope of the present invention.

Initially, the use of the terms "toothbrush," "electronic toothbrush," "sonic toothbrush," and the like are not meant to limit the scope of the present invention. Rather, the terms are used interchangeably and are meant to be merely illustrative in nature of certain aspects of the present invention.

In addition, the terms "output device," "digital media device," "video display," "audio display," and the like are not meant to limit the scope of the present invention. These terms are also used interchangeably and are meant to be merely illustrative in nature of certain aspects of the present invention.

Moreover, well known methods, procedures, and substances for both carrying out the objectives of the present invention and illustrating the preferred embodiment are incorporated herein but have not been described in detail as not to unnecessarily obscure aspects of the present invention.

Finally, while the foregoing description describes the preferred embodiment only in relation to a video display output, it will be appreciated by those of skill in the art that the invention described herein can be used with other portable media devices. Non-limiting examples include: MP3 players, Blackberry® devices manufactured by Research In Motion, Inc., iPod® music players, and the like. The following presents a detailed description of a preferred embodiment of the present invention.

Figure 1:
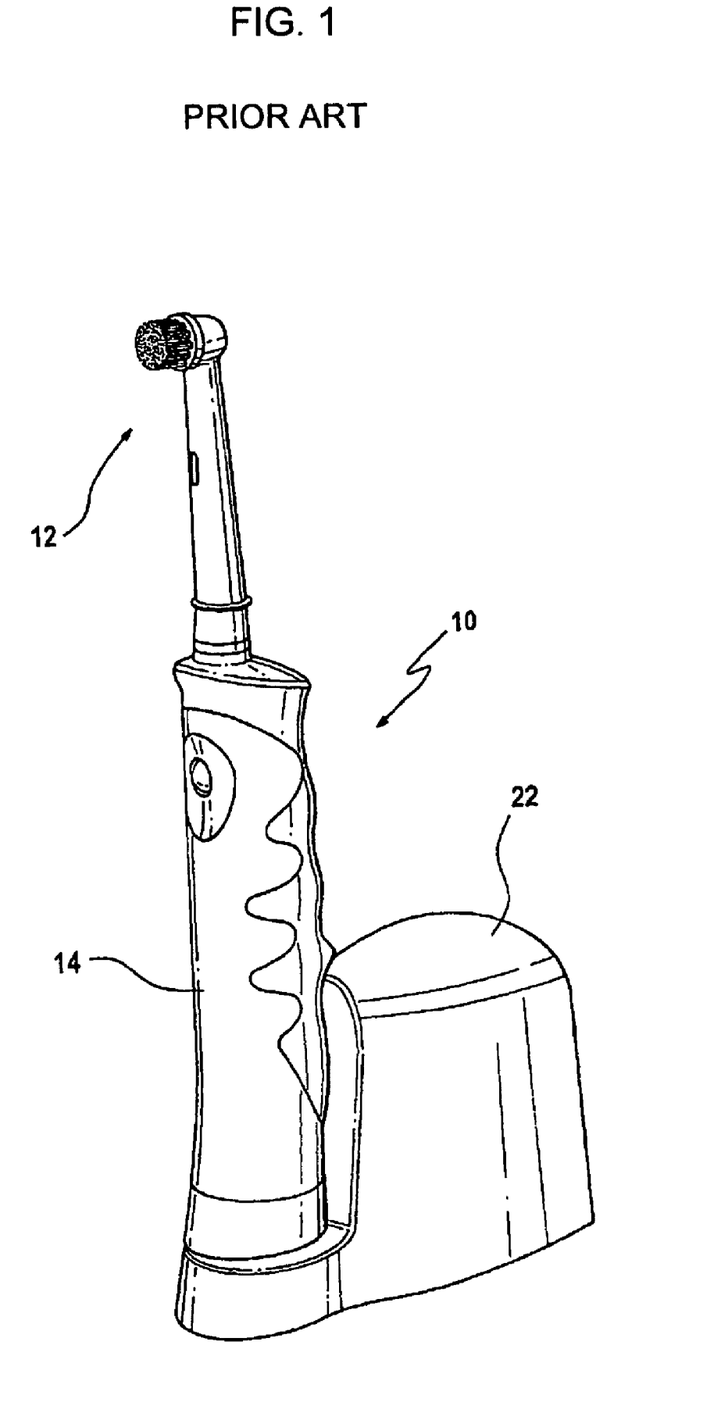
FIG. 1 is a prior art diagram of an electric toothbrush and charger.
Figure 2:
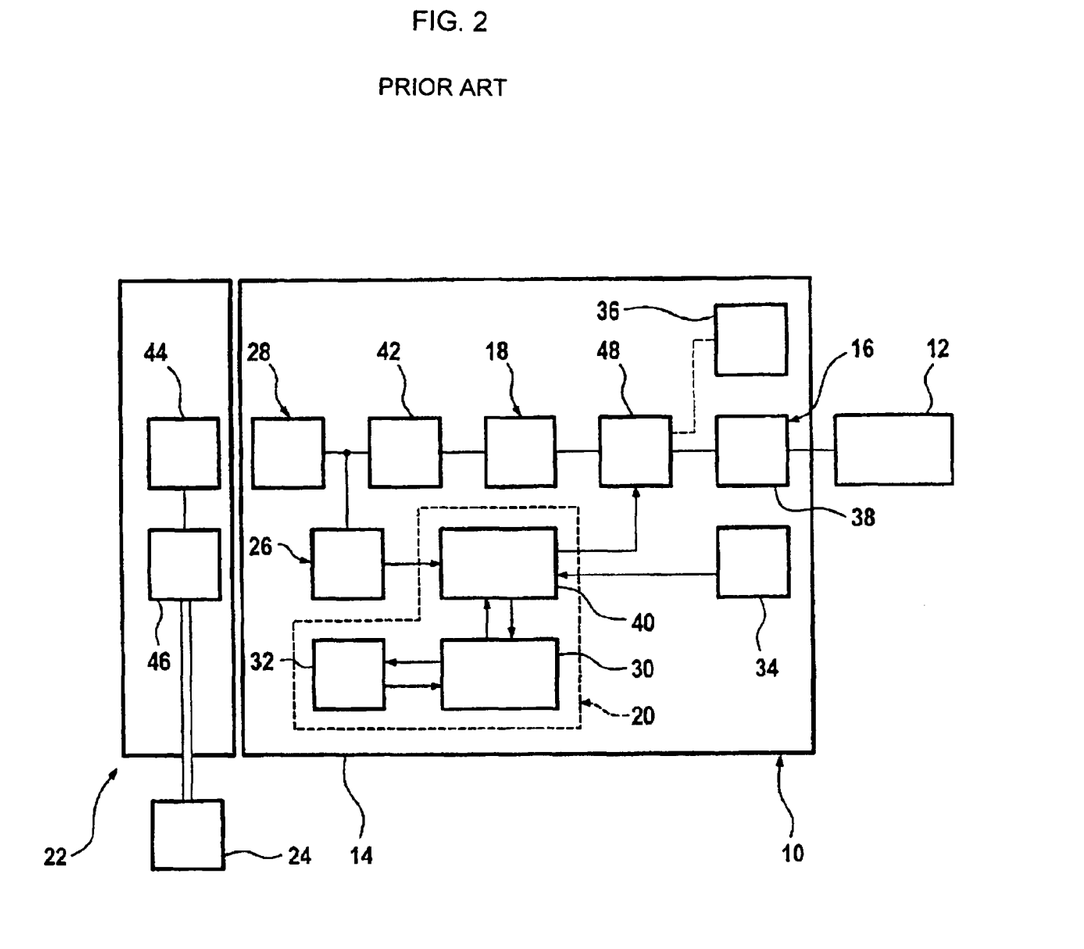
FIG. 2 is a prior art schematic illustration of a toothbrush with a charging station.

Referring to FIGS. 1-2, shown is a prior art toothbrush which can be utilized as a foundation upon which the improved toothbrush of the present invention can be constructed. Shown is prior art toothbrush 10 with a brush head 12 and casing 14. Casing 14 includes an electric motor 16, brush head 12, and battery 18.

Prior art toothbrush 10 optionally contains signal emitting means 20 and timer 34. Signal emitting means 20 can also contain signal transmitter 36 and loudspeaker 38 via a driver stage 48.

Prior art toothbrush 10 is coupled to charging station 22. Charging station 22 is connected to an electrical outlet 24. Charging station 22 has a charging control stage 46 that is connectable to electrical outlet 24, as well as connected transmitter coil 44. Transmitter coil 44 is inductively coupled with receiver coil 28 arranged in casing 14 so that electrical energy is transferred from transmitter coil 44 to receiver coil 28. Charging control means 42 is connected to receiver coil 28. As shown, charging control means 42, battery 18, driver stage 48, and electric motor 16 are electrically connected. The output signals from receiver coil 28 and signals from charging control means 42 are fed to sensor means 26. Sensor means 26 is connected to signal emitting means 20.

As is known, signal emitting means 20 further comprises memory means 30, random generator means 32, and a generator 40. Generator 40 is connected to driver stage 48.

Sensor means 26 detects a coupling and/or uncoupling between charging part 22 and casing 14, and activates signal emitting means 20. Sensor means 26 is sensitive to the temporal change in the charging current or charging voltage during the coupling and/or uncoupling of charging part 22 and casing 14.

When prior art toothbrush 10 is activated for tooth-cleaning, timer 34 is also activated. At the end of the cleaning procedure, prior art toothbrush 10 is deactivated and again placed or plugged back on charging station 22.

Figure 3:
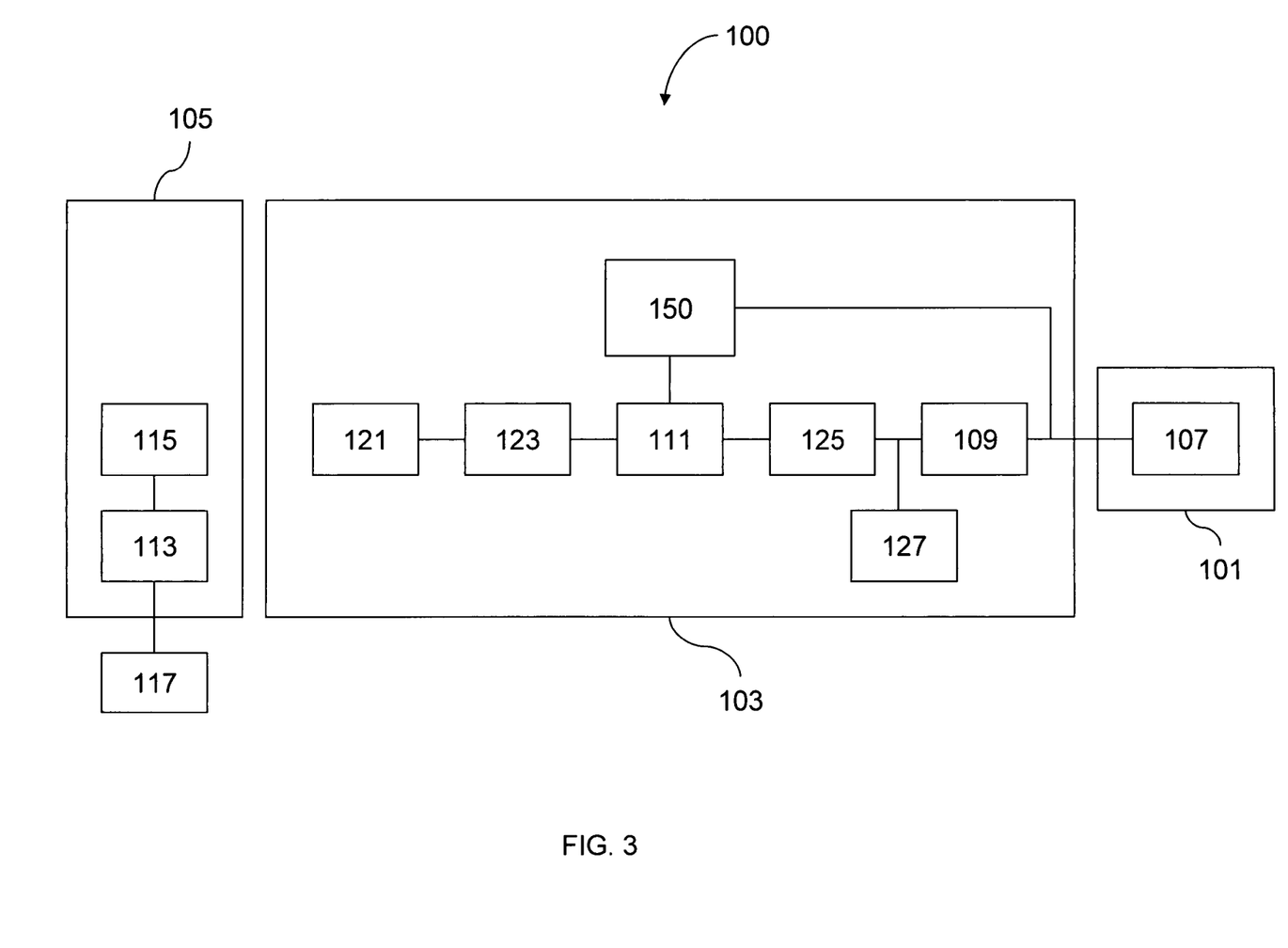
FIG. 3 is a schematic illustration of an electric toothbrush in accordance with the preferred embodiment of the present invention.

Referring next to FIG. 3, depicted is a schematic diagram of toothbrush 100 in accordance with the preferred embodiment of the present invention. Toothbrush 100 comprises brush head 101, housing 103, and base 105.

Brush head 101 can be any shape or type of brush head as is known in the art. Preferably, brush head 101 is detachable from housing 103. Brush head 101 can be detached by any means, however, it is preferred that brush head 101 further comprises a threaded portion (not shown). The threaded portion interacts with counter-threads disposed on housing 103. As a result, a user can screw in brush head 101. Advantageously, this allows a user to select from a plurality of brush heads.

Brush head 101 further comprises pressure sensor 107. Any pressure sensor as known in the art can be utilized. Preferably, pressure sensor 107 contains logic which can be programmed to store a preferred pressure range. In the preferred embodiment, the predetermined pressure range is as recommended by the American Dental Association. Of course, it is contemplated that the present invention can encompass any range of pressure ranges.

Housing 103 includes electric motor 109 and battery 111. Housing 103 can be comprised of any lightweight material such as plastic. In addition, housing 103 can contain from fitted indentations for easy gripping of the handle. Further, housing 103 can comprise an additional softer material such as rubber to aid in gripping toothbrush 100. Toothbrush 100 is coupled to charging station 105. Charging station 105 is connected to power source 117. In the preferred embodiment, power source 117 is an electrical outlet, however, it is contemplated that any power source can be utilized in accordance with the preferred embodiment. Charging station 105 comprises charging control stage 113 that is connected to power source 117 and transmitter coil 115. Transmitter coil 115 is inductively coupled with receiver coil 121 arranged in housing 103 so that electrical energy is transferred from transmitter coil 115 to receiver coil 121. Optionally, receiver coil 121 is electrically connected to charging control means 123. As shown, charging control means 123, battery 111, driver stage 125, and electric motor 109 are electrically connected.

Importantly, toothbrush 100 comprises transmitter 150. As shown, transmitter is disposed within housing 103. However, as is known in the art, transmitter 150 can be located on or near any part of toothbrush 100. In the preferred embodiment of the present invention, transmitter 150 is a wireless transmitter. By way of non-limiting examples, transmitter 150 can be any one of the following: a SM transmitter, an ISDN transmitter, an Ethernet transmitter, a CATV transmitter, a WiFi transmitter, a LAN transmitter, and a Bluetooth transmitter. In the preferred embodiment, transmitter 150 is a bluetooth transmitter. In the preferred embodiment, transmitter 150 is directly coupled to power source 111 because many wireless devices take several minutes to "power up." Attaching transmitter 150 directly to power source 111 ensures that transmitter 150 is capable of instantaneously transmitting signals when toothbrush 100 is activated.

When toothbrush 100 is activated for tooth-cleaning, timer 127, which is electrically connected to other components of the present invention, is activated. At the end of the cleaning procedure, toothbrush 100 is deactivated and again placed or plugged back on charging station 105. When a user applies pressure to his or her teeth using toothbrush 100, pressure sensor 107 measures the amount of force applied to the surface of teeth. If the pressure is within a predetermined range, a signal is sent to transmitter 150. The signal authorizes transmitter 150 to transmit the appropriate signal. In the preferred embodiment, transmitter 150 transmits a signal to an output device (not pictured) which turns the power to the output device on. Conversely, if an inappropriate amount of pressure is applied, pressure sensor 107 transmits a signal to transmitter 150 which causes transmitter 150 to cease transmitting. In alternative embodiments, pressure sensor 107 can be coupled to other components such as power source 111. In this manner, any function of toothbrush 100 can be controlled by pressure sensor 107.

Figure 4:
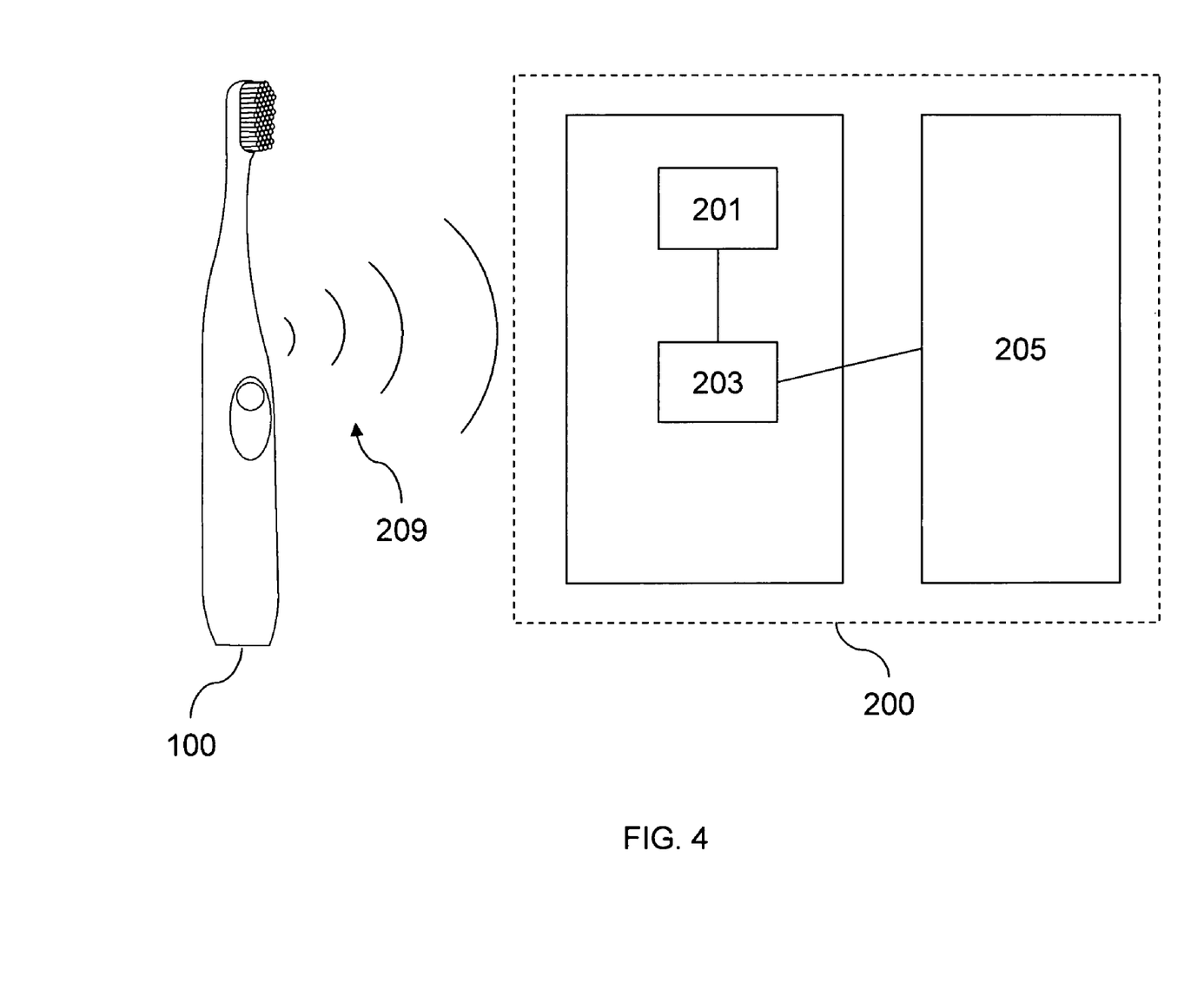
FIG. 4 is a diagram of the operation of the system of the present invention in accordance with the preferred embodiment.

Referring now to FIGS. 3-4, depicted is the use of toothbrush 100 in a system in accordance with the present invention. In operation, the user of electric toothbrush 100 first turns on a power switch (not shown) on housing 103 of electric toothbrush 100. Current from power source 111 is delivered to motor 109 which drives brush head 101. When a user begins brushing by applying the brush head to teeth, pressure sensor 107 measures the amount of force applied to a user's teeth. In this example, the pressure is within a predetermined range (i.e., the amount of force applied is appropriate). Pressure sensor 107 then sends a signal to transmitter 150 authorizing the transmission of a signal from transmitter 150. Transmitter 150 transmits a signal 209 to output device 200. The signal can comprise any data, however, in the preferred embodiment, signal 209 is an authorization to turn on output device 200.

Output device 200 can be any device capable of providing output to a user. Non-limiting examples include a cellular telephone, a portable digital assistant, a digital media storage device, a digital media playback device, a digital media transmitting device, a digital media receiving device, an iPod®, a Blackberry®, a television, a DVD player, a personal computer, a laptop computer, and a video game console system. Of course, any output device can be utilized in accordance with the present invention as long as it comprises receiver 201 and storage device 203.

Receiver 201 receives signal 209 from transmitter 150 and responds appropriately. Typically, signal 209 will initiate power in output device 200 and cause it to display output 205 from storage device 203. Storage device 203 can contain any output, including music, video, a video game, or combinations of audio and video. Storage devices are known in the art, and can comprise a memory card, a memory stick, a DVD, a video game cartridge, a DVR disk, or the like. In the preferred embodiment, displayed output 205 is displayed for the appropriate brushing time (e.g., two minutes).

Figure 5:
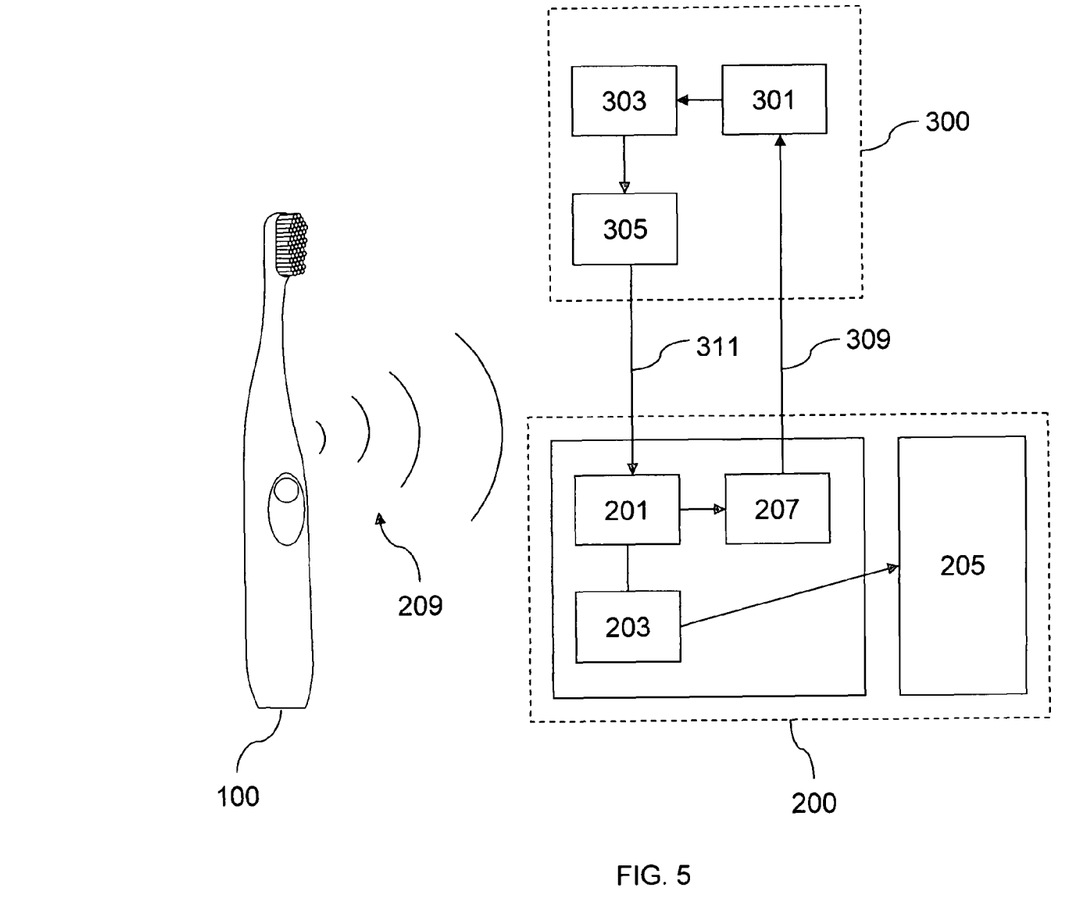
FIG. 5 is a diagram of an alternative example of a system in accordance with the present invention.

Referring now to FIGS. 3 & 5, depicted is an alternative toothbrush 100 system in accordance with the present invention. The user of electric toothbrush 100 first turns on a power switch (not shown) on housing 103 of electric toothbrush 100. Current from power source 111 is delivered to motor 109 which drives brush head 101. When a user begins brushing by applying the brush head to teeth, pressure sensor 107 measures the amount of force applied to a user's teeth. In this example, the pressure is within a predetermined range (i.e., the amount of force applied is appropriate). Pressure sensor 107 then sends a signal to transmitter 150 authorizing the transmission of a signal from transmitter 150.

Transmitter 150 transmits signal 209 to output device 200. The signal can comprise any data, however, in the preferred embodiment, signal 209 is an authorization to turn on output device 200.

Output device 200 can be any device capable of providing output to a user. Non-limiting examples include a cellular telephone, a portable digital assistant, a digital media storage device, a digital media playback device, a digital media transmitting device, a digital media receiving device, an iPod®, a Blackberry®, a television, a DVD player, a personal computer, a laptop computer, and a video game console system. Of course, any output device can be utilized in accordance with the present invention as long as it comprises receiver 201, storage device 203, and transmitter 207.

Receiver 201 receives signal 209 from transmitter 150 which initiates transmission of second signal 309 from transmitter 207 to remote database 300. Transmitter 207, like transmitter 150, can be any transmitter known in the art such as a SM transmitter, an ISDN transmitter, an Ethernet transmitter, a CATV transmitter, a WiFi transmitter, a LAN transmitter, and a Bluetooth transmitter. Signal 309 is received by receiver 301 associated with remote database 300. Receiver 301 is any commonly known receiver. In addition, remote databases are known in the art. Examples include a computer, a portable computer, and the like. Of course, any other remote database can be utilized in accordance with the preferred embodiment of the present invention. Receiver 301 is coupled to storage device 303, containing stored information. Storage device 303 can contain any output, including music, video, a video game, or combinations of audio and video. Storage devices are known in the art, and can comprise a memory card, a memory stick, a DVD, a video game cartridge, a DVR disk, or the like. Remote database 300 then transmits stored information 311 via transmitter 305 to storage device 203 which is associated with output device 200. Information can be stored temporarily or permanently as is known in the art. Information from storage device 203 is then displayed as output 205.

This embodiment advantageously allows output device 200 to be pre-programmed with a variety of downloadable content. A user can customize the content to be viewed during the tooth brushing process. In addition, an important aspect of the present invention is that transmitter 150 of toothbrush 100 will cease transmitting at any point in which pressure sensor 107 determines that an inappropriate amount of force is applied to the teeth (i.e., the brushing technique is inappropriate). When transmission 209 ceases, output device 200 ceases to display output 205. Because the user is interested in the content of displayed output 205, the user is motivated to brush properly to ensure that he or she can enjoy displayed output 205.

What is claimed is:

1. A tooth cleaning system, comprising:
   a toothbrush having a brush head, a pressure sensor and a transmitter, said pressure sensor being positioned on said brush head so as to measure the amount of pressure applied by a user to user's teeth, said transmitter being coupled to said pressure sensor for transmitting a signal when the pressure measured by said pressure sensor is within a predetermined range;
   an output device having a receiver for receiving the signal from said transmitter, said output device being configured to play back a pre-recorded multimedia recording in response to the receipt of the signal by said receiver, said transmitter being configured to cease the transmission of the signal to said receiver and to thereby cause said output device to cease the playback of said pre-recorded multimedia recording when the pressure measured by said pressure sensor is outside said predetermined range, whereby said pre-recorded multimedia recording is played back only when the measured pressure is within said predetermined range so as to motivate the user to use said toothbrush properly, and said transmitter being configured to resume the transmission of the signal to said receiver and to thereby cause said output device to resume the playback of said pre-recorded multimedia recording when the pressure measured by said pressure sensor falls within said predetermined range; and
   a remote database including a plurality of pre-recorded multimedia recordings, said remote database being configured to communicate with said output device so as to transmit one of said plurality of pre-recorded multimedia recordings to said output device, said pre-recorded multimedia recording played back by said output device being said one of said plurality of pre-recorded multimedia recordings.

2. The system of claim 1, wherein said output device includes a second transmitter; and wherein said remote database includes a third receiver and a third transmitter.

3. The system of claim 2, wherein said second transmitter of said output device is configured to transmit a second signal to said third receiver of said remote database in response to the receipt of said signal transmitted from said transmitter of said toothbrush by said receiver of said output device.

4. The system of claim 3, wherein said third transmitter of said remote database is configured to transmit said one of said plurality of pre-recorded multimedia recordings to said output device in response to the receipt of said second signal by said third receiver of said remote database.

5. The system of claim 1, wherein said toothbrush has a motor and a power source, said brush head being coupled to said motor, said transmitter being electrically coupled to said power source.

6. The system of claim 5, wherein said power source includes a rechargeable battery.

7. The system of claim 6, further comprising a charging station connectable to a second power source, said toothbrush being configured to be coupled to said charging station so as to charge said rechargeable battery of said toothbrush.

8. The system of claim 1, wherein said toothbrush includes a housing, said transmitter being disposed within said housing.

9. The system of claim 1, wherein said output device is one of a cellular telephone, a portable digital assistant, a digital media storage device, a digital media playback device, a digital media transmitting device, a digital media receiving device, a television and a computer.

10. The system of claim 1, wherein said transmitter includes one of an SM transmitter, an ISDN transmitter, an Ethernet transmitter, a CATV transmitter, a WiFi transmitter, a LAN transmitter and a Bluetooth transmitter.

11. The system of claim 1, wherein said transmitter includes a wireless transmitter.

* * * * *